(12) United States Patent
Nishimura et al.

(10) Patent No.: US 8,053,246 B2
(45) Date of Patent: Nov. 8, 2011

(54) METHOD OF ESTERIFYING BIO-RELATED MOLECULE FOR MASS SPECTROMETRY AND METHOD OF MASS SPECTROMETRY OF OBTAINED ESTERIFIED DERIVATIVE

(75) Inventors: Shin-Ichiro Nishimura, Sapporo (JP);
Yoshiaki Miura, Sapporo (JP)

(73) Assignee: National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 12/224,310

(22) PCT Filed: Feb. 22, 2007

(86) PCT No.: PCT/JP2007/053312
§ 371 (c)(1),
(2), (4) Date: Dec. 3, 2008

(87) PCT Pub. No.: WO2007/099856
PCT Pub. Date: Sep. 7, 2007

(65) Prior Publication Data
US 2009/0311793 A1    Dec. 17, 2009

(30) Foreign Application Priority Data
Feb. 23, 2006 (JP) .................................. 2006-046173

(51) Int. Cl.
*G01N 24/00* (2006.01)
*G01N 33/544* (2006.01)
(52) U.S. Cl. ......... 436/173; 436/524; 436/528; 436/161
(58) Field of Classification Search .................. 436/173, 436/524, 528, 161
See application file for complete search history.

(56) References Cited

U.S. PATENT DOCUMENTS
5,510,084 A *   4/1996   Cros et al. ...................... 422/104

FOREIGN PATENT DOCUMENTS
JP     05-279327 A    10/1993
JP     2005-148054 A   6/2005

OTHER PUBLICATIONS
Smerdka et al., Polymer-bound Alkyltriazenes for Mild Racemization-free Esterification of Amino Acid and Peptide Derivatives, 2004, J. Peptide Sci., 603-611.*

(Continued)

*Primary Examiner* — Krishnan S Menon
*Assistant Examiner* — Allison M Gionta
(74) *Attorney, Agent, or Firm* — Jacobson Holman PLLC (57) ABSTRACT

To provide a method for enhancing analysis sensitivity of bio-related molecules in mass spectrometry. To provide a method for rapidly and conveniently analyzing biological acid molecules using the method of enhanced analysis sensitivity in mass spectrometry.

A method of preparing a bio-related molecule to be subjected to mass spectrometry, in which at least a part of acid group(s) is esterified, comprising reacting a bio-related molecule comprising an acid group(s) with a triazene compound to esterify at least a part of said acid group(s). A method of analyzing bio-related molecules comprising reacting a bio-related molecule comprising an acid group(s) with a triazene compound to esterify said acid group(s), and then subjecting said bio-related molecule having an esterified acid group(s) to mass spectrometry.

11 Claims, 4 Drawing Sheets

OTHER PUBLICATIONS

E. H. White et al., 1-Methyl-3-p-Tolyltriazene and its se in the Esterification of Acids, Organic Syntheses, Coll. vol. 5, p. 797, 1973); vol. 48, p. 102, 1968.*

Udiavar et al, The Use of Multidimensional Liquid-Phase Separations and Mass Spectrometry for the Detailed Characterization of Posttranslational Modifications in Glycoproteins, 1998, Anal. Chem. 70, 3572-3578.*

Dalluge, J. J., Mass spectrometry for direct determination of proteins in cells: applications in biotechnology and microbiology, 2000, Fresenius J Anal Chem, 366, 701-711.*

Amino Acids, Chem4Kids.com, 2001, accessed Dec. 3, 2009 online.*

STN Database Registry entry for 3-methyl-p-tolyltriazene.*

Yamada et al., High performance polymer supports for enzyme-assisted synthesis of glycoconjugates, Carbohydrate Research, 305, 1998, 443-461.*

Powell et al., "Stabilization of Sialic Acids in N-linked Oligosaccharides and . . . "; Rapid Communications in Mass Spectromerty, vol. 10, No. 9, 1996, pp. 1027-1032.

Irie et al., "Gas chromatographic-ho ni yoru Cyclopropanecarbon sanrui no Teiryo", Nippon Nogei Kagaku Kaishi, vol. 53, No. 10, 1979, pp. 337-342.

Shackleton, et al. "Gas chromatographic and mass spectrometric analysis of urinary acidic metabolites of cortisol." Steroids, vol. 36, No. 3, Sep. 1980, pp. 289-298.

Erb et al. "Polymer-supported triazenes as smart reagents for the alkylation of carboxylic acids." Chemistry, vol. 9, No. 11, Jun. 6, 2003, pp. 2582-2588.

Zaia. "Mass spectrometry of oligosaccharides." Mass Spectrometry Reviews, vol. 23, No. 3, May 2004, pp. 161-227.

Lohse et al. "Solid-phase oligosaccharide Tagging (SPOT): validation on glycolypid-derived structures." Angewandte Chemie, vol. 118, Jun. 2006, pp. 4273-4278.

Miura et al. "Rapid and simple solid-phase esterification of sialic acid residues for quantitative glycomics by mass spectrometry." Chemistry, vol. 13, No. 17, 2007, pp. 4797-4804.

* cited by examiner

METHOD OF ESTERIFYING BIO-RELATED MOLECULE FOR MASS SPECTROMETRY AND METHOD OF MASS SPECTROMETRY OF OBTAINED ESTERIFIED DERIVATIVE

This is a 371 of PCT/JP2007/053312 filed Feb. 22, 2007.

TECHNICAL FIELD

The present invention relates to a method of esterifying bio-related molecules for mass spectrometry using a triazene compound and to a method of mass spectrometry employing the resulted esterified derivatives.

The present invention relates to techniques relating to novel and simple derivatization to enhance the analysis sensitivity in the field of natural science research, more particularly, in mass spectrometry of bio-related molecules such as proteins, peptides, nucleic acids, and saccharide chains.

BACKGROUND ART

Attempts have been made to overcome problems such as decreased sensitivity and the generation of degradation products of acidic molecules among bio-related molecules in mass spectrometry (MS). In particular, methods of esterification and amidation to inhibit the removal of sialic acid from sialic acid-containing oligosaccharide chains have been reported. For example, Japanese Unexamined Patent Publication (KOKAI) No. 2005-148054 (Patent Reference 1) describes a method for the label amidation of bio-related molecules. However, no method exists for simply, highly efficiently, and rapidly modifying acidic groups in bio-related molecules on a solid phase surface.

Patent Reference 1: Japanese Unexamined Patent Publication (KOKAI) No. 2005-148054

DISCLOSURE OF INVENTION

Problems to Be Solved by Invention

In mass spectrometry, since cleavage often occurs preferentially at the sites of aspartic acid and glutamic acid residues in the tandem mass spectrometry (MS/MS) of proteins or peptides, it is difficult to obtain fragment ions that have cleaved at the sites of other amino acid residues. Accordingly, there are problems in that the overall fragment ion detection rate is poor and analysis is difficult.

In the mass spectrometric measurement of sialic acid-containing saccharide chains, sialic acid dissociation tends to occur in the ion isolation step due to in-source decay (ISD), post-source decay (PSD), ion trapping, and the like. Thus, the absolute quantity of the targeted ion decreases and the quantity of the molecule produced by dissociation undergoes a relative increase, failing to accurately reflect the mixture ratio. Further, the dissociation of sialic acid occurs preferentially in MS/MS analysis of sialic acid-containing saccharide chains, making it difficult to obtain other fragment ions in quantities adequate for analysis.

A similar problem to the above, originating in structural phosphoric acid diester bonds, exists in the mass spectrometry of nucleic acid (DNA or RNA) molecules.

Accordingly, the object of the present invention is to provide a method for improving the stability of bio-related molecules and enhancing analysis precision and analysis sensitivity in mass spectrometry. A further object of the present invention is to provide a method for rapidly and conveniently analyzing biological acid molecules using a method of enhanced analysis precision and sensitivity in mass spectrometry.

Means of Solving the Problem

The present invention is as set forth below:

[1] A method of preparing a bio-related molecule to be subjected to mass spectrometry, in which at least a part of acid group(s) is esterified, comprising reacting a bio-related molecule comprising an acid group(s) with a triazene compound to esterify at least a part of said acid group(s).

[2] A method of analyzing bio-related molecules comprising reacting a bio-related molecule comprising an acid group(s) with a triazene compound to esterify said acid group(s), and then subjecting said bio-related molecule having an esterified acid group(s) to mass spectrometry.

[3] The method in accordance with [1] or [2], wherein said acid group is at least one member selected from the group consisting of carboxyl groups, phosphoric acid groups and sulfonic groups.

[4] The method in accordance with any one of [1] to [3], wherein said bio-related molecule is at least one member selected from the group consisting of proteins, peptides, saccharides, conjugated saccharides, and nucleic acids.

[5] The method in accordance with any of [1] to [4], wherein said triazene compound is denoted by the following general formula:

[Chem. 1]

(wherein X denotes an aryl group, substituted aryl group, hetaryl group, or substituted hetaryl group, and R denotes an alkyl, cycloalkyl, allyl, or benzyl.)

[6] The method in accordance with any of [1] to [5], wherein said triazene compound is 3-methyl-1-(p-tolyl)triazene.

[7] The method in accordance with any of [1] to [6], wherein said triazene compound is a compound labeled with a stable isotope.

[8] The method in accordance with [7], wherein said stable isotope of labeled compound is based on heavy hydrogen, heavy carbon, or heavy nitrogen.

[9] The method in accordance with any one of [1] to [8], wherein the esterification of said acid group(s) is conducted for substantially the entire quantity of acid group(s).

[10] The method in accordance with any one of [1] to [9], further comprising the steps of:
immobilizing a bio-related molecule comprising an acid group(s) on a solid phase support in advance by means of a covalent bond or noncovalent bond prior to conducting said esterification;
esterifying and after esterification, recovering the esterified bio-related molecule from the solid phase; and
subjecting the recovered esterified bio-related molecule to mass spectrometry.

[11] The method in accordance with any one of [1] to [9], wherein the bio-related molecule comprising an acid group(s) is esterified in a free state, and following esterification, the esterified bio-related molecule in the esterification reaction mixture is subjected to mass spectrometry as is or the esterified bio-related molecule in the esterification reaction mixture is purified and then subjected to mass spectrometry.

[12] The method in accordance with any one of [1] to [11], wherein said mass spectrometry is mass spectrometry with MALDI-TOF MS or MALDI-TOF MS/MS.

[13] The method in accordance with any one of [1] to [11], wherein said mass spectrometry is based on liquid chromatography electrospray ionization—mass spectrometry (LC-ESI-MS or LC-ESI-MS/MS).

Effect of the Invention

The present invention provides a method permitting the rapid and convenient esterification of a bio-related molecule, and in particular, provides a method enhancing the analysis precision and sensitivity of mass spectrometry of bio-related molecules by employing a method of esterification on a solid phase. The present invention further provides a method of qualitative and quantitative analysis of bio-related molecules using a method of enhancing analysis precision and sensitivity in mass spectrometry. Still further, the present invention yields a stable isotope-labeled compound from a bio-related molecule through the action of a triazene compound such as heavy hydrogen-labeled 3-methyl-$d_3$-1-(p-tolyl)triazene. This compound permits multiple specimen mass spectrometry, including simultaneous comparative determination with light hydrogen compounds.

BEST MODE FOR CARRYING OUT THE INVENTION

The first aspect of the present invention is a method of preparing a bio-related molecule to be subjected to mass spectrometry, in which at least a part of acid group(s) is esterified, comprising reacting a bio-related molecule comprising an acid group(s) with a triazene compound to esterify at least a part of said acid group(s).

The second aspect of the present invention is a method of analyzing a bio-related molecule comprising reacting a bio-related molecule comprising an acid group(s) with a triazene compound to esterify said acid group(s), and then subjecting said bio-related molecule having an esterified acid group(s) to mass spectrometry.

The esterification is the same in the first and second aspects of the present invention, and will be described below.

[Esterification]

The bio-related molecule that is subjected to esterification in the present invention comprises an acid group(s). The acid group(s) is(are) not specifically limited other than that it(they) be a functional group(s) present on the bio-related molecule and exhibit acidity. Examples of such functional groups are groups selected from among the group consisting of carboxyl groups, phosphoric acid groups, and sulfonic acid groups. Depending on the type of bio-related molecule, there will be a case either where one of the above-listed acid groups be present or where a plurality of the above-listed acid groups be present.

The bio-related molecule subjected to esterification in the present invention is not specifically limited other than that it comprises an acid group(s). Examples of such bio-related compounds are molecules selected from the group consisting of proteins, peptides, saccharides, conjugated saccharides, and nucleic acids.

Specific examples of proteins are 1) proteins contained in biological samples (blood serum, cells, tissue, urine, or the like) obtained from healthy or diseased humans; 2) proteins found in plants and in animals other than humans; and 3) recombinant proteins artificially produced by genetic recombination procedures. Proteins from the above-listed group that have been subjected to operation such as chemical modification are also included.

Specific examples of peptides are those obtained by limiting digestion of proteins obtained by subjecting samples containing proteins from the above-listed protein group to the effects of a (group of) proteolytic enzyme(s).

Examples of oligosaccharides or glycans are the group of carbohydrate compounds composed of various monosaccharides that are widely encountered in the natural world, as well as those derived from biological samples or prepared in the laboratory. More specific examples are oligosaccharides derived glycoconjugates and compounds comprising free glycan chains such as heparin and hyaluronic acid.

More specific examples of conjugated saccharides are biomolecules comprising saccharide chains such as glycoproteins, glycolipids, proteoglycans, and phosphatidyl anchors.

More specifically, "nucleic acid" is a collective term for the group of organic compounds having constituent components in the form of nucleic acid bases, such as DNA, RNA, cDNA, or oligonucleotides and assuming a linked form by means of phosphodiester bonds.

The triazene compound employed in esterification in the present invention can be a compound denoted by the general formula below:

[Chem. 2]

(wherein X denotes an aryl group, substituted aryl group, hetaryl group, or substituted hetaryl group, and R denotes an alkyl, cycloalkyl, allyl, or benzyl.)

For example, X denotes an aryl group, substituted aryl group, hetaryl group, or substituted hetaryl group. Examples of aryl groups are phenyl and naphthyl groups. Examples of substituted aryl groups are tolyl groups. The term "hetaryl group" refers to a heteroaromatic group such as a pyridyl or thienyl group. An example of a substituted hetaryl group is a 2-aminopyridine group. Desirably, X is a phenyl group substituted with an atom or group of atoms functioning as an electron donor in the para-position of the triazenyl group. An example of an atom functioning as an electron donor is such as oxygen, and an example of an atom group functioning as such is —NH—.

R is selected from the group consisting of alkyl, cycloalkyl, allyl, and benzyl groups. More specifically, a C1 to C4 alkyl or benzyl group is desirable, with R preferably denoting a compound labeled with a stable isotype in the form of hydrogen, carbon, nitrogen, or the like.

Examples of triazene compounds are 3-methyl-1-(p-tolyl)triazene, 3,3-bis(aminoethyl)-1-hydroxy-2-oxo-1-triazene, 3,3-dimethyl-1-(3-nitrophenyl)triazene, and 3-ethyl-3-(ethylaminoethyl)-hydroxy-2-oxo-1-triazene. These triazene compounds are commercially available.

The triazene compound can be a compound labeled with a stable isotope. The stable isotope label can be heavy hydrogen, heavy carbon, or heavy nitrogen, for example. An example of a triazene compound labeled with a stable isotope is 3-methyl-$d_3$-1-(p-tolyl)triazene and the like.

The triazene compound labeled with a stable isotope can be synthesized by a known method. For example, employing a synthesis method similar to the method described in the following reference document, an intermediate in the form of a diazonium salt can be subjected to the action of heavy hydrogen-labeled methylamine ($CD_3NH_2$) to synthesize 3-methyld$_3$-1-(p-tolyl)triazene (Reference Document: White, E H, Baum, A A, and Eitel, D E, Organic Synthesis, Coll. Vol. 5, p. 797; Vol. 48, p. 102, "1-Methyl-3-p-tolyltriazene and its use in the esterification of acids").

Specifically, the esterification of the acid group(s) can be conducted under the following conditions:

(1) The quantity ratio of the triazene compound to the bio-related compound is normally such that the triazene compound is suitably supplied to the reaction in a quantity of about 100 to 1,000-fold.

(2) A solvent can be employed in esterification of the acid group(s). For example, in an esterification reaction on a solid phase, a high yield can be obtained in acetonitrile, a 1:1 mixture of dimethyl sulfoxide (DMSO)—acetonitrile, or dioxane. In a reaction in a solution, for example, the use of a 1:1 mixture of dimethyl sulfoxide (DMSO)—acetonitrile as reaction solvent causes the reaction to progress at high yield.

(3) The reaction can be conducted at a temperature of from room temperature to 60° C., for example. However, an adequate reaction can normally be conducted at 37° C.

(4) The reaction can be adequately conducted for from 30 minutes to one hour while maintaining the temperature.

(5) The presence of moisture is undesirable for the reaction; the solid phase can be cleaned with acetonitrile prior to the reaction to substitute solvent, and the reaction can be conducted in acetonitrile. Additionally, when esterifying a free sialic acid-containing saccharide chain in a solution, for example, the reaction does not progress adequately in pure acetonitrile. Good reactivity is achieved by admixing 50 percent DMSO, for example, into the reaction solvent. Thus, the use of a mixed reaction solvent of acetonitrile and DMSO is desirable.

The above acid group esterification is suitably conducted for essentially the entire quantity of acid group(s). In esterification employing a triazene compound in the present invention, essentially the entire quantity of acid group(s) is readily esterified by taking the above into consideration and controlling the ratio of the triazene compound to the bio-related molecule, the reaction temperature, the reaction time, and the like.

In the present invention, the above-mentioned esterification is conducted after immobilizing a bio-related molecule comprising an acid group(s) on a solid phase support in advance by means of a covalent bond or noncovalent bond; the esterified bio-related molecule is recovered from the solid phase following esterification; and the recovered esterified bio-related molecule can be subjected to mass spectrometry.

The bio-related molecule having an acid group(s) can be adsorbed or immobilized as follows.

A bio-related sample being subjected to measurement is adsorbed by a procedure following the usual method of applying sequential phases onto the surface of a solid phase such as silica gel, aminopropyl silica gel (such as Sep-Pak NH2, made by Waters), or polyamide resin (such as Discovery DPA-6S made by Supelco). Bio-related samples of high polarity can be readily adsorbed onto the surface of a support employed in solid phase extraction such as set forth above in a system in which a large amount of an organic solvent such as acetonitrile is present.

When the sample being subjected to measurement is a free saccharide chain, a reducing end of the free saccharide chain can be immobilized on the surface of a commercially available solid phase support having a hydrazide group or aminooxy group. For example, beads on which hydrazide groups are supported in advance, such as Affi-Gel Hz, Bio-Rad, can be employed. The sample containing the saccharide chain molecule can be reacted with the beads in an acidic to neutral buffer solution by the usual methods and immobilized on the beads. Following the esterification reaction, the saccharide chains can be recovered by conducting an acid treatment of a degree that does not degrade the saccharide chain molecule. Alternatively, the saccharide chains can be recovered by imine exchange reaction with an excess of low-molecular-weight aminooxy or hydrazide compound.

When the sample being subjected to measurement is a free peptide or nucleic acid molecule, any one of methods (a) to (d) below may be employed.

(a) After introducing a thiol group onto the 5' or 3' end of a nucleic acid such as DNA, RNA, or an oligonucleotide using a commercially available kit, it can be immobilized with a disulfide bond to the activated thiol group of Thiopropyl Sepharose 6B made by Pharmacia. Similar application to the serine or threonine residue of a protein or peptide is also possible, so use in immobilizing proteins and peptides is also possible. A cysteine residue in a protein or peptide can also be employed for direct immobilization.

(b) After labeling the 5' or 3' end of a nucleic acid such as DNA, RNA, or an oligonucleotide with biotin using a commercially available kit, it can be immobilized on avidin-bound beads. Since the amino groups or thiol groups of proteins and peptides can be readily labeled with biotin, avidin-bound beads can also be used to immobilize proteins and peptides.

(c) A particular molecule group can also be immobilized by combining (a) and (b) above. That is, after introducing a thiol group, the action of a biotin molecule having a functional group such as a thiol group-reactive maleimide can be used to label with biotin the hydroxyl group of the particular bio-sample, permitting immobilization on avidin-bound beads.

(d) A thiol group can be introduced with a commercially available reagent onto the amino group of a protein or peptide, which can then be immobilized with a disulfide bond to the activated thiol group of Thiopropyl Sepharose 6B made by Pharmacia.

The esterified bio-related molecule can be recovered from the solid phase following esterification as follows. 1) When immobilized on the solid phase by means of a disulfide bond, release is achieved by means of a neutral buffer solution containing 50 to 100 mM dithiothreitol while maintaining the mixture at room temperature for 30 minutes, after which the bio-related molecule is recovered by centrifugation or filtration. 2) When immobilized by an avidin—biotin interreaction, particularly in the case of monomeric avidin, release is achieved by heating the bio-related molecule in a 5 mM biotin solution, after which it is recovered by centrifugation or filtration.

Mass spectrometry of the esterified bio-related molecule that has been recovered will be described further below.

In the present invention, a bio-related molecule comprising an acid group(s) can be esterified in a free state, an esterified bio-related molecule can be isolated from the esterification reaction mixture following esterification, and the isolated esterified bio-related molecule can be used in mass spectrometry.

The procedure for esterifying a bio-related molecule comprising an acid group(s) in a free state is as set forth above. When necessary, excess reagent can be removed as follows from the esterification reaction mixture following esterification. For example, in the case of a free saccharide chain or free peptide, after washing away unreacted reagent and DMSO by silica gel solid phase extraction, the target compound that is bound to the support can be eluted and recovered with a 50 percent acetonitrile aqueous solution. The recovery can also be done with a silica based support or a graphatized carbon resin (such as Carbograph resin, from Alltech).

[Mass Spectrometry]

In the present invention, the structure of the bio-related molecule that has been esterified by the above-described method is analyzed by mass spectrometry. The equipment employed in mass spectrometry can be suitably selected based on the type of bio-related molecule being handled. Taking into account the fact that bio-related molecules are macromolecules, mass spectrometry is desirably conducted by MALDI-TOF MS, MALDI-TOF MS/MS, LC-ESI-MS, or LC-ESM-MS/MS (a liquid chromatography electrospray ionization—mass spectrometry device). MS denotes a mass spectrometer and MS/MS denotes tandem (two linked) mass spectrometers.

Embodiments

The present invention will be described in greater detail below through embodiments.

Embodiment 1

An experiment was conducted to confirm by mass spectrometry that methyl esterification could be conducted on an insoluble support using 3-methyl-1-(p-tolyl)triazene (MTT) on an albumin-derived N-type saccharide chain sample.

An albumin-derived N-type saccharide chain sample was prepared by the method of Seko et al. and the saccharide chain was liberated by the usual method based on PNGase F (Seko A, Koketsu M, Nishizono M, Enoki Y, Ibrahim H R, Juneja L R, Kim M, Yamamoto T. Occurrence of a sialylglycopeptide and free sialylglycans in hen's egg yolk. Biochim Biophys Acta. 1997 Apr. 17: 1335 (1-2): 23-32).

Silica gel beads (Iatrobead, Iatron Laboratories) were employed as the solid phase support. A one µL quantity of about 1 mM free saccharide chain aqueous solution was added to an equivalent quantity of 10 mM HCl and the mixture was diluted with a 20-fold quantity of acetonitrile. The mixture was placed on a silica gel bead column that had been equilibrated with acetonitrile in advance and washed with acetonitrile. The outlet of the column was capped, a suitable quantity of 100 mM MTT solution (1:1 DMSO/aceto-nitrile) was added, and the mixture was maintained at 37° C. for one hour. Following the reaction, the cap was removed, washing was conducted with acetonitrile, and washing was conducted with acetonitrile solution containing 4 percent water. The saccharide chains were eluted from the column with a 50 percent acetonitrile aqueous solution and analyzed by MALDI-TOF MS.

Figure 1:
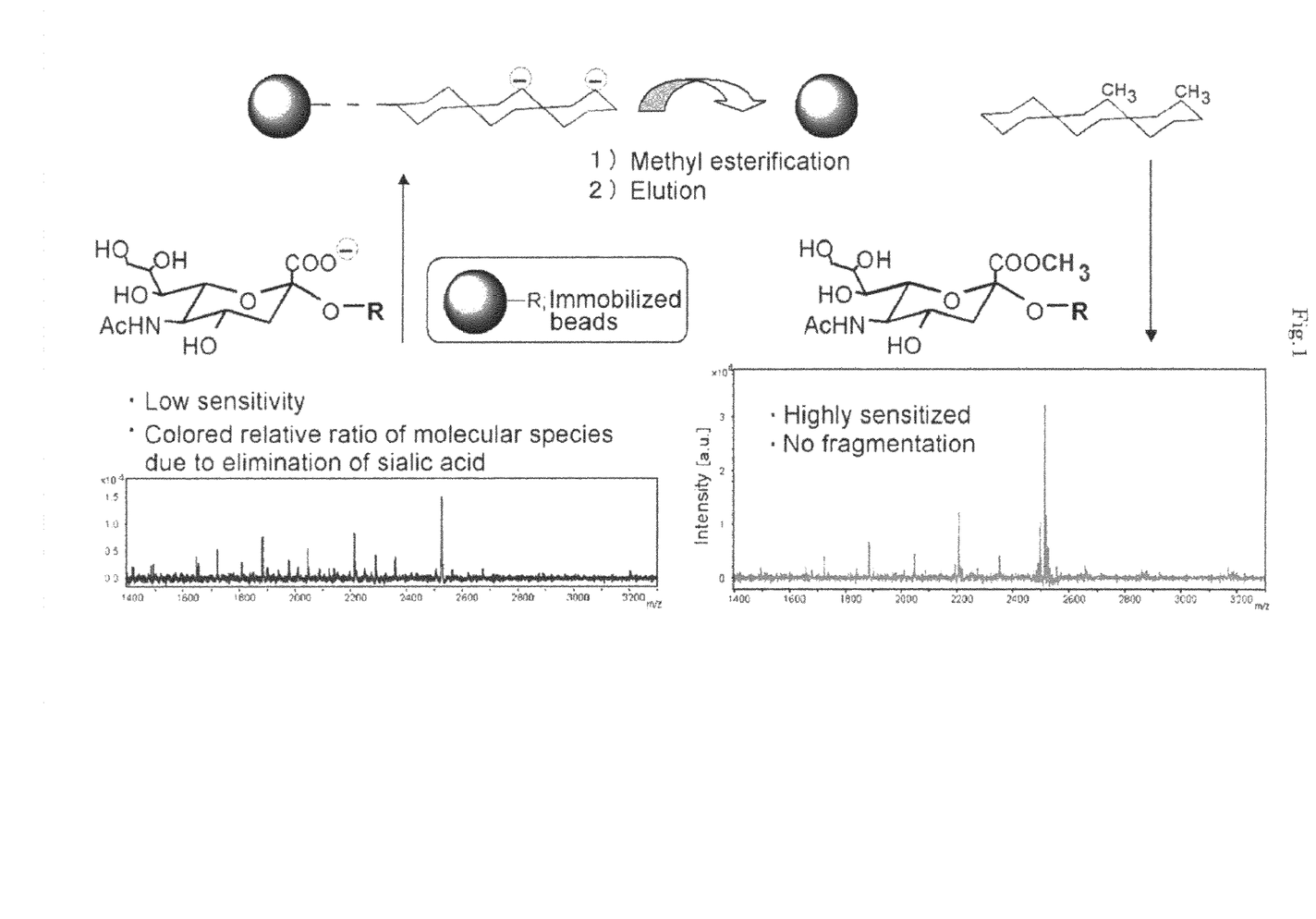
FIG. 1 shows a schematic of the method of Embodiment 1.

FIG. 1 shows the reaction scheme. All N-type saccharide chains from the serum sample and the like are selectively immobilized on the beads. After the negative charge of the sialic acid has been eliminated by methyl esterification, all the saccharide chains in the serum are liberated and recovered. Through immobilization on a solid phase, impurities, reaction reagents and the like are readily washed away, achieving purification, highly sensitive detection, and maintenance of the relative ratios of the saccharide chain molecule species present.

Mass Spectrometry by MALDI-TOF MS

Figure 2:
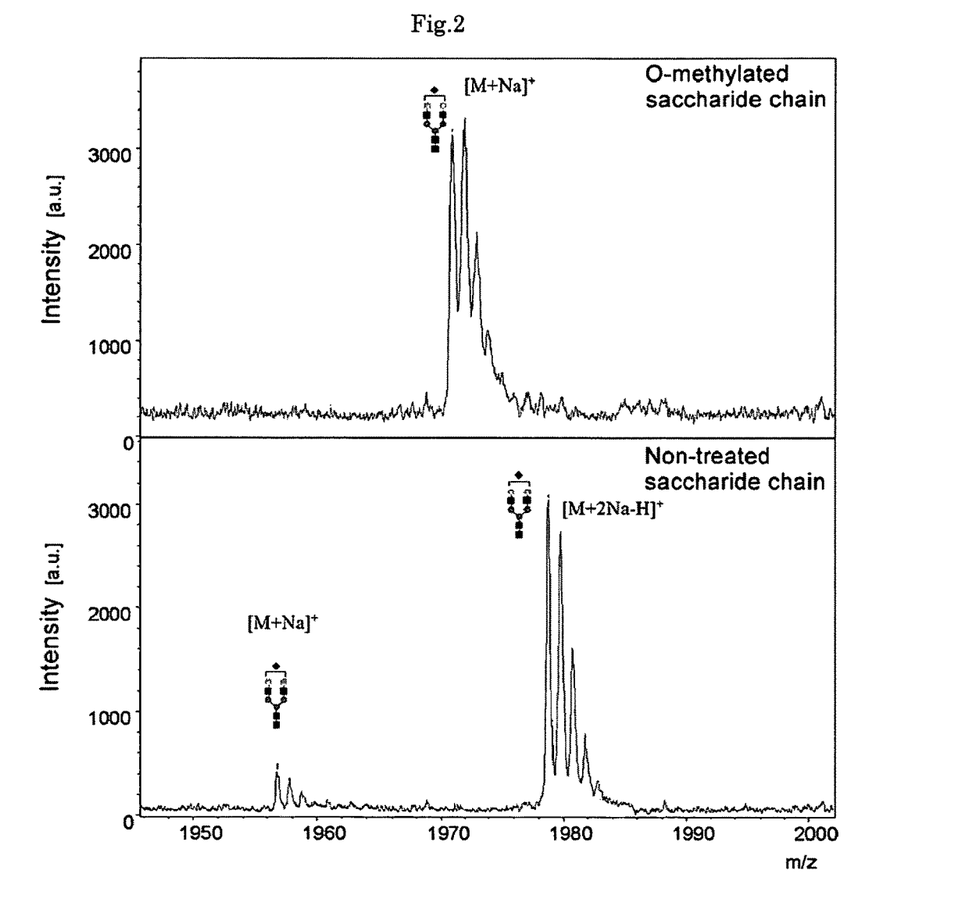
FIG. 2 shows the results of mass spectrometric analysis of albumin-derived saccharide chains in Embodiment 1.

FIG. 2 shows the results of mass spectrometry conducted on separately prepared serum saccharide chains that were not subjected to the methyl esterification and serum saccharide chains that were subjected to the methyl esterification. When untreated (lower figure), the two peaks of $[M+Na]^+$ and $[M+2Na-H]^+$ are detected. By contrast, when treated by methyl esterification (upper figure), a simple analysis result of just $[M+Na]^+$ was achieved, indicating enhancement of sensitivity and precision. The fact that the peaks in the untreated sample did not remain also showed that the esterification reaction had adequately progressed in a short period.

This indicated that the esterification of the saccharide chains enhanced the analysis precision and sensitivity of mass spectrometry.

According to the present invention, the acid charge of acid group(s) can be rapidly and conveniently neutralized by introducing an ester as part of the common sample preparation steps of synthesis, separation, purification, and the like of a biomolecule employing a solid phase. By eliminating the acid charge, it is possible to overcome various problems and enhance the analysis precision and sensitivity of mass spectrometry.

According to the present invention, it is also possible to anticipate that highly precise and highly sensitive analysis in mass spectrometry will become possible for glycosaminoglycans and nucleic acid-related molecules that have thus far defied ready analysis. Major improvement in SNPs analysis by mass spectrometry is also anticipated.

Embodiment 2

Gold nanoparticles (GCNP) were used as an insoluble support and sialic acid-containing oligosaccharides that had been immobilized on GCNP were methyl esterified with MTT. An experiment was conducted by mass spectrometry to determine their usefulness.

After supporting Galβ1,4 GlcNAc (LacNAc) disaccharide on GCNP with covalent bonds, recombinant rat α2,6-sialyltransferase was maintained at 37° C. for 24 hours in 50 mM cacodylic acid buffer (pH 6.0, 0.5 percent Trion CF-54) in the presence of 800 µM CMP-N-acetylneuramic acid (CMP-Neu5Ac), yielding GCNP supporting sialic acid-containing oligosaccharide. Following the reaction, cleaning was conducted with deionized water and purification was conducted by ultrafiltration with a YM-50 made by Millipore.

The sialic acid-containing GCNP was dissolved in 5 µL of deionized water, and the solution was mixed with 1 µL of 50 mM hydrochloric acid and 200 µL of acetonitrile. Following centrifugation, drying was conducted, 5 µL of 0.2 M MTT solution (DMSO-acetonitrile, 1:1) was added, and the mixture was maintained at 60° C. for 1.5 hours. Following the reaction, 10 µL of deionized water was added, and the reagent and solvent were removed by a centrifugal operation. The GCNP in the residue and the sialic acid-containing GCNP that had not been subjected to MTT treatment were analyzed by MALDI-TOF MS.

Mass Spectrometry by MALDI-TOF MS

Figure 3:
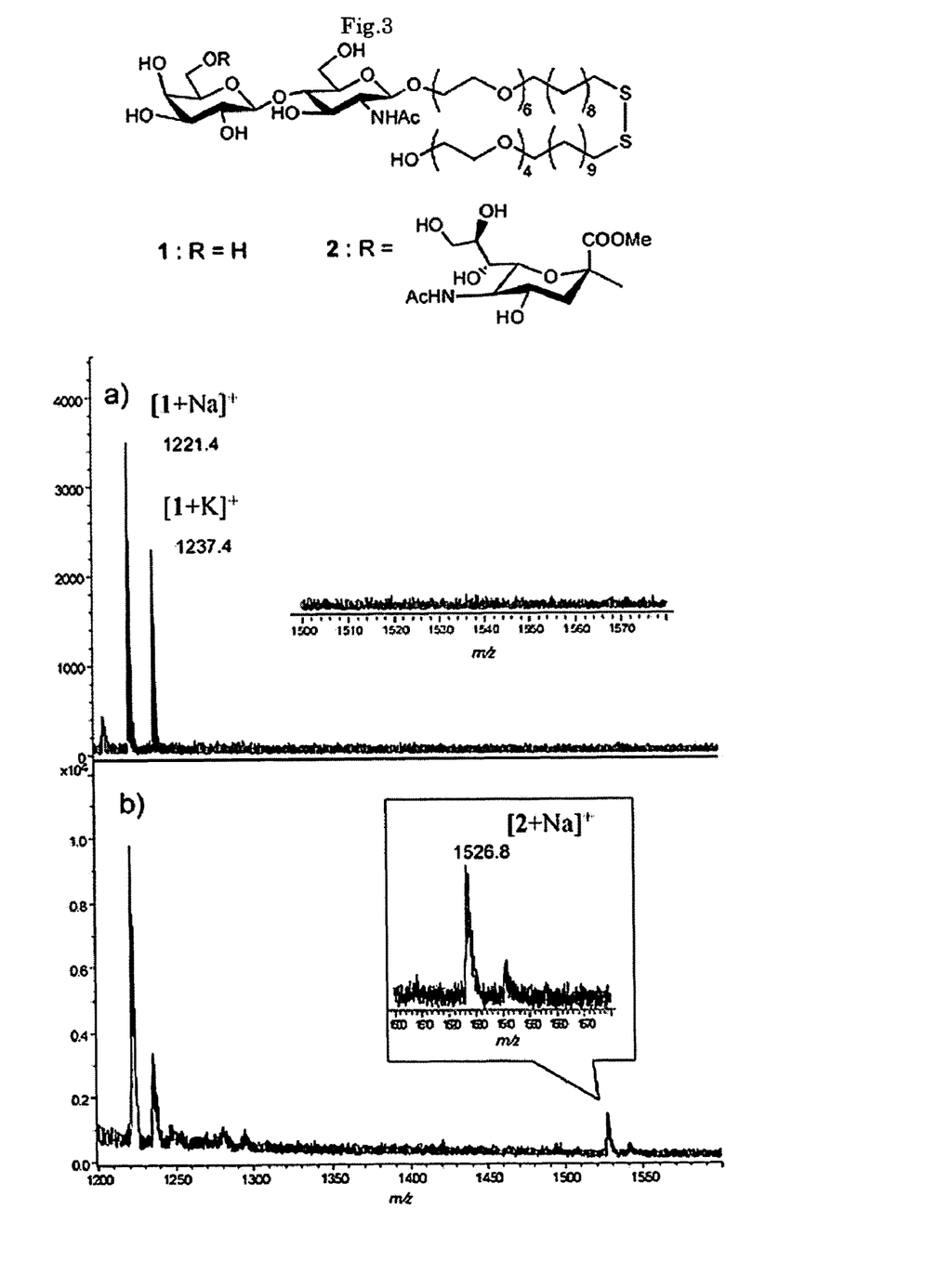
FIG. 3 shows mass spectrometric spectra of MTT treated and untreated samples obtained in Embodiment 2.

FIG. 3 shows the mass spectrometry spectra of MTT-treated and untreated samples. In the untreated sample (upper figure, a), the peak of the targeted trisaccharide could not be detected due to the low sensitivity to sialic acid-containing oligosaccharide and the dissociation of sialic acid. By contrast, in the sample treated with MTT, a peak derived from the targeted methyl esterified trisaccharide (lower figure, b $[2+Na]^+$) was stably detected at an m/z of 1526.

The above experiment results indicated that methyl esterification by MTT occurred on gold nanoparticles as well, that the sensitivity and reliability of mass spectrometry was enhanced, and in combination with the results of Embodiment 1, that the present invention was broadly applicable irrespective of the insoluble support.

Embodiment 3

An example of the application of methyl esterification of peptide carboxylic acid will be given.

Silica gel beads were employed as an insoluble support. A trypsin degradation product of transferrin (Tf) was provided as a model peptide. Following the methyl esterification with MTT of Tf peptide immobilized on silica gel, an experiment was conducted to confirm the methyl esterification reaction by mass spectrometry.

The usual method was utilized to hydrolyze Tf with trypsin to peptides, 10 µL of degradation product was mixed with 10 µL of 0.1 M hydrochloric acid, and 400 µL of acetonitrile was added. Silica gel (50 µL) was packed in a spin column and equilibrated with acetonitrile, after which the mixture was added. After removing the unreacted material by centrifugation, the mixture was washed with acetonitrile in a centrifugal operation. A 50 µL quantity of 0.1 M MTT solution (DMSO-acetonitrile, 1:1) was added and the mixture was maintained for 1 hour at 60° C. Following the reaction, 400 µL of acetonitrile was added and the reagent and solvent were removed by a centrifugal operation. Next, centrifugal washing was conducted with 96 percent acetonitrile aqueous solution, and the peptide was eluted out of the silica gel with 50 µL of 50 percent acetonitrile aqueous solution. Peptide degradation product in the eluate and peptide degradation product that had not been treated with MTT were analyzed by MALDI-TOF MS.

Mass Spectrometry by MALDI-TOF MS

Figure 4:
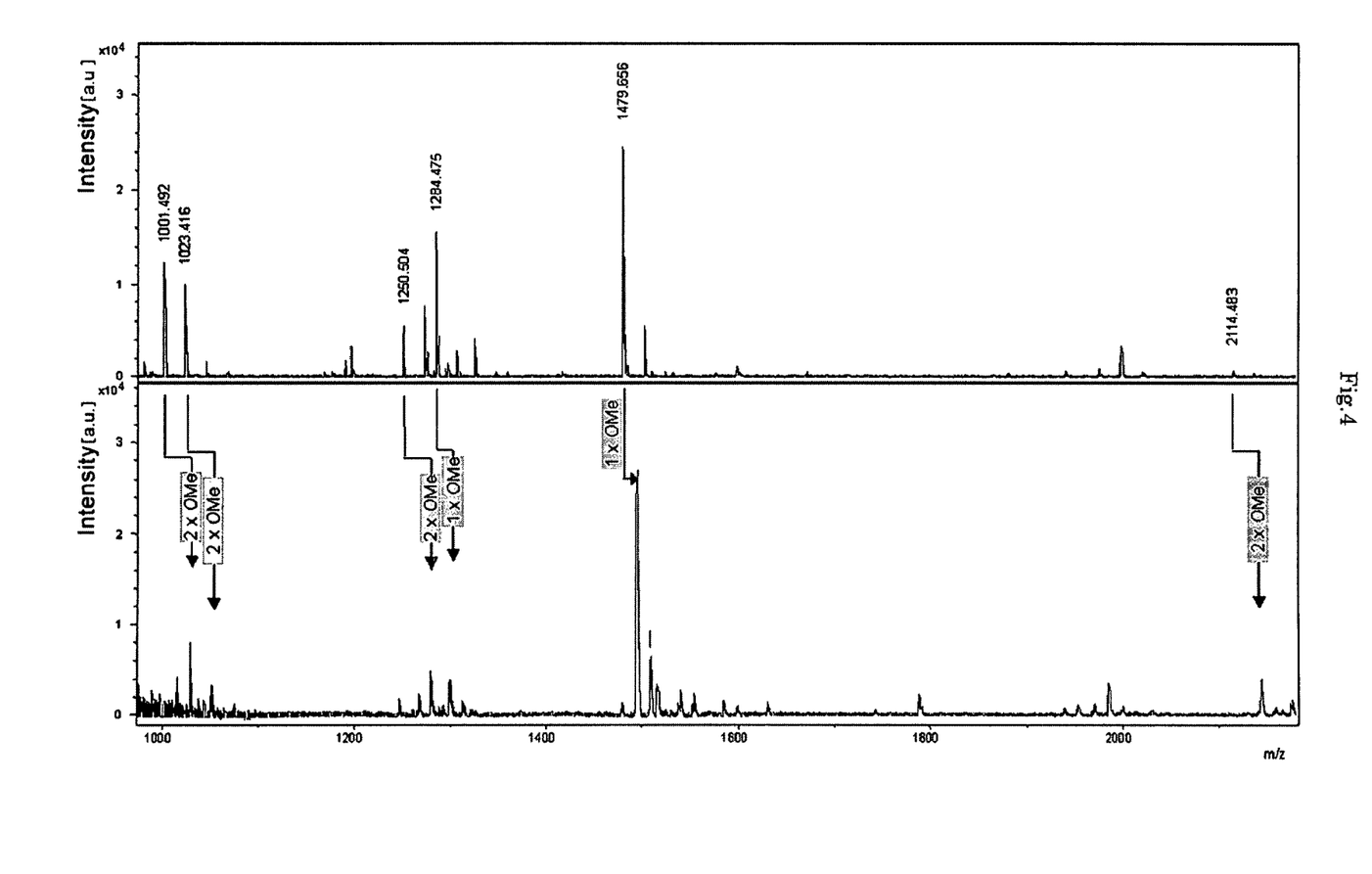
FIG. 4 shows mass spectrometric spectra of MTT treated and treated samples obtained in Embodiment 3.

FIG. 4 shows the mass spectrometric spectra of MTT-treated and untreated samples. Among the peptides observed in the untreated sample (upper figure), a typical methyl esterification product is shown in the lower figure of FIG. 4. Peptides were detected as methyl esterified molecules those were estimated based on the quantity of glutamic acid or aspartic acid in the peptide sequence.

The above-described experiment results indicated that according to the present invention using MTT, methyl esterification of the carboxylic acids in a peptide sequence was possible.

INDUSTRIAL APPLICABILITY

The esterification method of the present invention can be introduced into a high-throughput analysis system employing automated robots, and can be used for the labeling agents of labeling kits for various bio-related molecules. It can be applied to nucleic acid-related molecules the mass spectrometric analysis of which has conventionally been difficult, as well as to high-throughput base sequencing by mass spectrometry.

The invention claimed is:

1. A method of analyzing bio-related molecules comprising
    immobilizing a bio-related molecule comprising a free saccharide chain, having a reducing end, and an acid group(s) on a solid phase support, having a hydrazide group or aminooxy group, in advance by means of covalent bond formation between the reducing end and the hydrazide group or aminooxy group;
    reacting the immobilized bio-related molecule comprising a saccharide chain and an acid group(s) with a triazene compound denoted by the following general formula to esterify said acid group(s), wherein the triazene compound is denoted by the general formula wherein X denotes an aryl group, substituted aryl group, hetaryl group, or substituted hetaryl group, and R denotes an alkyl, cycloalkyl, allyl, or benzyl;
    recovering the bio-related molecule, having an esterified acid group(s), from the solid phase; and then
    subjecting the recovered bio-related molecule, having an esterified acid group(s), to mass spectrometry.

2. The method in accordance with claim 1, wherein said acid group(s) is at least one member selected from the group consisting of carboxyl groups and phosphoric acid groups.

3. The method in accordance with claim 1, wherein said bio-related molecule is at least one member selected from the group consisting of conjugated saccharides.

4. The method in accordance with claim 1, wherein said triazene compound is 3-methyl-1-(p-tolyl)triazene.

5. The method in accordance with claim 1, wherein said triazene compound is a compound labeled with a stable isotope.

6. The method in accordance with claim 5, wherein said stable isotope of labeled compound is based on heavy hydrogen, heavy carbon, or heavy nitrogen.

7. The method in accordance with claim 1, wherein the esterification of said acid group(s) is conducted for substantially the entire quantity of acid group(s).

8. The method in accordance with claim 1, wherein said mass spectrometry is mass spectrometry with MALDI-TOF MS or MALDI-TOF MS/MS.

9. The method in accordance with claim 1, wherein said mass spectrometry is based on liquid chromatography electrospray ionization—mass spectrometry (LC-ESI-MS or LC-ESI-MS/MS).

10. The method in accordance with claim 3, wherein said conjugated saccharides are selected from the group consisting of glycoproteins, glycolipids, proteoglycans, and phosphatidyl anchors.

11. The method in accordance with claim 3, wherein said bio-related molecule is a sialic-acid containing oligosaccharide or a sialic-acid containing saccharide chain.

* * * * *